United States Patent [19]

Nanmori et al.

[11] Patent Number: 5,188,956
[45] Date of Patent: Feb. 23, 1993

[54] THERMOSTABLE AMYLASE

[75] Inventors: Takashi Nanmori, Neyagawa; Ryu Shinke, Hyogo, both of Japan

[73] Assignee: Showa Denka K.K., Tokyo, Japan

[21] Appl. No.: 619,803

[22] Filed: Nov. 21, 1990

Related U.S. Application Data

[63] Continuation of Ser. No. 374,795, Jul. 3, 1989, abandoned.

[30] Foreign Application Priority Data

Jul. 1, 1988 [JP] Japan ................................. 63-165762

[51] Int. Cl.$^5$ .......................... C12N 9/24; C12N 9/26; C12N 9/28; C12N 9/34
[52] U.S. Cl. ...................................... 435/200; 435/95; 435/201; 435/202; 435/204; 435/205; 435/832
[58] Field of Search ................... 435/95, 99, 201, 202, 435/206, 832, 205, 204, 200

[56] References Cited

U.S. PATENT DOCUMENTS

| | | | |
|---|---|---|---|
| 4,113,509 | 9/1978 | Leach et al. | 435/202 |
| 4,284,722 | 8/1981 | Tamuri et al. | 435/99 |
| 4,493,893 | 6/1985 | Mielenz | 435/201 |
| 4,578,352 | 3/1986 | Katkocin et al. | 435/202 |
| 4,600,693 | 6/1986 | Kindle et al. | 435/202 |
| 4,613,570 | 9/1986 | Zeman | 435/202 |
| 4,642,288 | 2/1987 | DeMiguel et al. | 435/202 |
| 4,647,538 | 3/1987 | Zeikus et al. | 435/201 |

FOREIGN PATENT DOCUMENTS

| | | |
|---|---|---|
| 0171218 | 2/1986 | European Pat. Off. . |
| 0200095 | 11/1986 | European Pat. Off. . |
| 60-83595 | 5/1985 | Japan . |
| 61-47189 | 3/1986 | Japan . |
| 61-260881 | 11/1986 | Japan . |
| 63-59881 | 3/1988 | Japan . |
| 63-59887 | 3/1988 | Japan . |

OTHER PUBLICATIONS

Biochem Abs. 89-09224 Kim et al AEMIDF Appl. Enviro Microbiol (1989) 55, 6 1638-39.
Biotech Abs 86-043731/07 Abs Jackson et al. EP-171218.
Starch/Starke, vol. 36, No. 12, 1984, pp. 405-411, "Properties and Application of a Thermostable Maltogenic Amylase Produced by a Strain of Bacillus Modified by Recombinant-DNA Techniques".
Patent Abstracts of Japan, vol. 11, No. 282 (C-446) (2729), Sep. 11, 1987 & JP-AS-62 79 783 (Showa Sangyo K.K.) Apr. 13, 1987.
Chemical Abstracts, vol. 111, No. 1, Jul. 3, 1987, p. 5882, Abstract No. 5881h, "Isolation of Thermostable Alpha-Amylase by Immunoreaction with Bacterial Anti--Beta-Amylase Serum".
Partial European Search Report.

Primary Examiner—Herbert J. Lilling
Attorney, Agent, or Firm—Sughrue, Mion, Zinn, Macpeak & Seas

[57] ABSTRACT

A thermostable amylase having the following properties: (1) Action: acting on raw starch to produce mainly maltose and matotriose; (2) Optimum pH: about 6.0; (3) Stable pH: after incubation at a pH of 5 to 8 for one hour at 22° C., the residual activity thereof is at least 95%; (4) Optimum temperature: 70° C.; (5) Thermostability: the enzyme is not substantially inactivated by incubation at 60° C. or 70° C. for 15 minutes; and after incubation at 70° C. for one hour, the residual activity thereof is at least 90%; (6) Molecular weight: 52,000±5,000 as determined by gel filtration; a process for production of the amylase using *Bacillus stearothermophilus*; and a process for production of maltooligosaccharide comprising mainly maltose and maltotriose, comprising the steps of treating raw starch with a thermostable amylase which acts on raw starch, at a temperature lower than a temperature at which the raw starch is gelatinized to hydrolyze the starch and thereby form maltooligosaccharides comprising mainly maltose and maltotriose; and recovering the maltooligosaccharides.

2 Claims, 3 Drawing Sheets

THERMOSTABLE AMYLASE

This is a continuation of application Ser. No. 07/374,795 filed Jul. 3, 1989, abandoned.

BACKGROUND OF THE INVENTION

1. Field of the invention

The present invention relates to a thermostable amylase, a process for the production thereof, a microorganism producing amylase, and a process for the production of maltooligosaccharides using the amylase.

2. Description of the Related Art

Oligo saccarides derived from starch, such as maltose, maltotriose, and the like, are used in various fields; most widely in the food industry, due to their superior properties as a base material for food production and a sweetening agent. Further, the demand for purified maltose as an ingredient of transfusion liquids has also increased, due to the superior properties thereof when compared with the conventionally used glucose. There is also an increasing demand for an oligosaccharide mixture containing maltotriose, obtained as a byproduct of the production of a purified maltose, having a mild sweetness and a viscosity lower than conventionally used syrups mainly comprising dextrin.

In a conventional process for the production of starch-hydrolyzation products, for example, oligosaccharides such as maltose, maltotriose and the like, raw starch is suspended in water at a high density, the starch suspension is heated to a temperature of between 85° C. and 120° C. to gelatinyze the suspension and form a starch paste having a high viscosity, the starch paste is treated with a starch-liquefying enzyme such as α-amylase, to lower the viscosity thereof by a partial cleavage of the starch chain, and the liquefied starch solution is treated with a saccharifying enzyme such as glucoamylase, β-amylase or the like, depending on a desired product. In this conventional process, the gelatinyzing process and liquefying process require a large amount of energy. Moreover, due to the high viscosity of the starch paste, the gelatinyzing process and liquefying process require special apparatuses, and thus the cost of production of the final product is high. Furthermore, the liquefaction of the starch paste at a high temperature stimulates the aging of the liquefied starch and provides an isomerization of reducing terminal glucose residues of the liquefied starch, both of which result in a decreased yield of a final product.

To solve these problems, attempts have been made to directly treat raw starch with an enzyme having the ability to hydrolyze raw starch, and omitting the gelatinyzing and liquefying steps. For example, a method has been proposed in which a non-steaming alcohol fermentation process has been attempted wherein a saccharifying enzyme having a strong ability to hydrolyze raw starch is used. But this process is not practically useful.

Regarding enzymes which hydrolyze raw starch, Japanese Unexamined Patent Publication (Kokai) Nos. 60-83595 and 61-83595 disclose a raw starch-hydrolyzing glucoamylase produced by a fungus belonging to the genus Aspergillus; Japanese Unexamined Patent Publications (Kokai) Nos. 63-59881 and 63-59887 disclose a strong raw starch-hydrolyzing ability in the presence of α-amylase, provided by a raw starch-hydrolyzing enzyme produced by a fungus belonging to the genus Penicillum: and Japanese Unexamined Patent Publication (Kokai) No. 61-47189 discloses a raw starch-hydrolyzing glucoamylase produced by a fungus belonging to the genus Humicola.

In the saccharification of raw starch using a raw starch hydrolizing enzyme, taking into consideration the saccharification rate and a prevention of contamination by microorganisms, the enzyme should act on the raw starch at a temperature lower than a temperature at which raw starch is gelatinyzed, but higher than a temperature at which contaminating microorganisms can grow. More specifically, the raw starch hydrolyzing enzyme should act at 45° C. to 70° C., more preferably 55° C. to 65° C. But β-amylases which act on raw starch and are stable at such temperatures are not known.

As enzymes which hydrolyze starch to provide maltose, β-amylase of plant origin, for example, barley β-amylase, and soybean β-amylase, are conventionally used, but in addition to the above problems of thermostability, β-amylases of plant origin also pose the problem of a stable supply thereof in a sufficient amount. Therefore, a β-amylase of microbial origin, which is thermostable and is readily available in amounts sufficient for industrial use, is urgently needed, but β-amylases of microbial origin which meet the requirements of industry are not known, although various kinds of β-amylase of microbial origin have been reported.

A common disadvantage among conventional β-amylases is that, since β-amylases cannot hydrolize the α-1,6 glycoside bond in starch, a debranching enzyme such as isoamylase, pullulanase, or the like must be used in combination with the β-amylase to provide a satisfactory yield. These debranching enzymes, however, are expensive.

SUMMARY OF THE INVENTION

Accordingly, the present invention provides a novel enzyme which can hydrolyze raw starch to produce malto oligosaccharides mainly comprising maltose and maltotriose at a yield of substantially 100%, without using a debranching enzyme, at a temperature which is lower than a temperature at which raw starch is gelatinyzed but high enough to prevent the growth of contaminating organisms.

More specifically, the present invention provides a thermostable amylase having the following properties:

(1) Acting on raw starch to produce mainly maltose and maltotriose;
(2) Optimum pH: about 6.0;
(3) Stable pH: after incubation at a pH of 5 to 8 for one hour at 22° C., residual activity is at least 95%;
(4) Optimum temperature: 70° C.;
(5) Thermostability: the enzyme is not substantially inactivated by incubation at 60° C. or 70° C. for 15 minutes; and after incubation at 70° C. for one hour, the residual activity thereof is at least 90%;
(6) Molecular weight: 52,000±5,000 as determined by gel filtration.

The present invention also provides a thermostable amylase produced by *Bacillus stearothermophilus* and having the following properties:

(1) Acting on raw starch to produce mainly maltose and maltotriose;
(2) Optimum pH: about 6.0;
(3) Optimum temperature: 70° C.;
(4) Molecular weight: 52,000±5,000.

Further, the present invention provides a microorganism strain of *Bacillus stearothermophilus* capable of producing the above-mentioned thermostable amylase.

Still further, the present invention provides a process for the production of malto-oligosaccharides comprising mainly maltose and maltotriose, comprising the steps of treating raw starch with a thermostable amylase which acts on raw starch, at a temperature lower than a temperature at which the raw starch is gelatinized, to hydrolyze the starch and thereby form maltooligosaccharides comprising mainly maltose and maltotriose; and recovering the maltooligosaccharides.

BRIEF DESCRIPTION OF THE INVENTION

DESCRIPTION OF THE PREFERRED EMBODIMENTS

The present enzyme, amylase, has the following properties.

(1) Action:

The present amylase acts on raw starch to produce mainly maltose and maltotriose. In particular, when this amylase acts on raw starch at 60° C., the hydrolysis thereby of raw starch is substantially 100%. The ease of hydrolysis of various raw starches of different origins by the present enzyme is on the order of; wheat starch->corn starch->sweet potato starch->potato starch (see FIG. 1).

Moreover, the present thermostable amylase having an ability to hydrolyze raw starch also has a strong adsorption to the various kinds of raw starch, which strong adsorption is responsible for the outstanding hydrolysis thereby of the raw starch.

Figure 2:
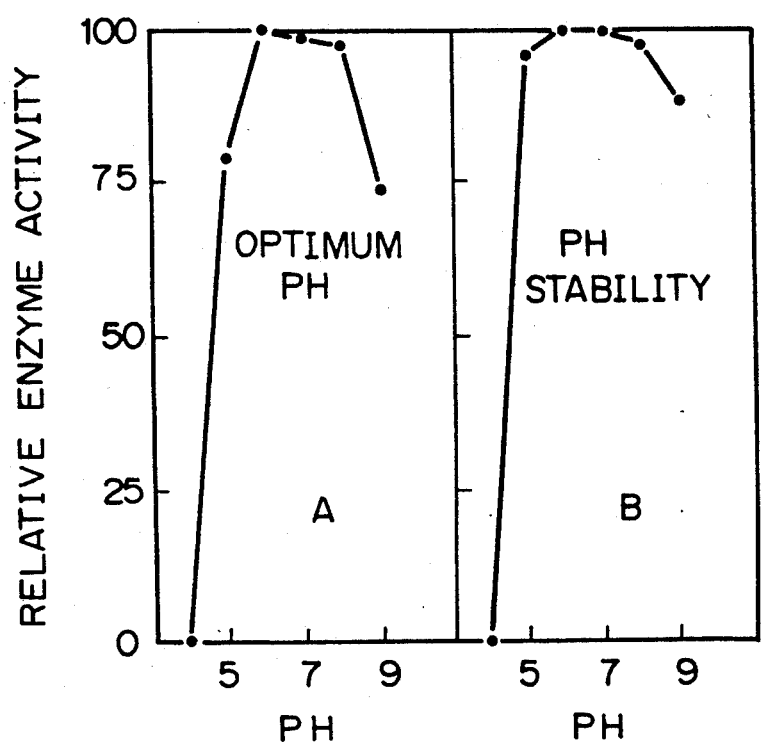
FIG. 2 shows graphs of the optimum pH and stable pH range of the present enzyme.

(2) Optimum pH and stable pH:

The present enzyme has an optimum pH of about 6.0, as shown in FIG. 2A. Where the present enzyme is treated at various pH for one hour at 22° C., the enzyme shows a residual activity of at least 95% at a pH value of 5 to 8, as shown in FIG. 2B.

Figure 3:
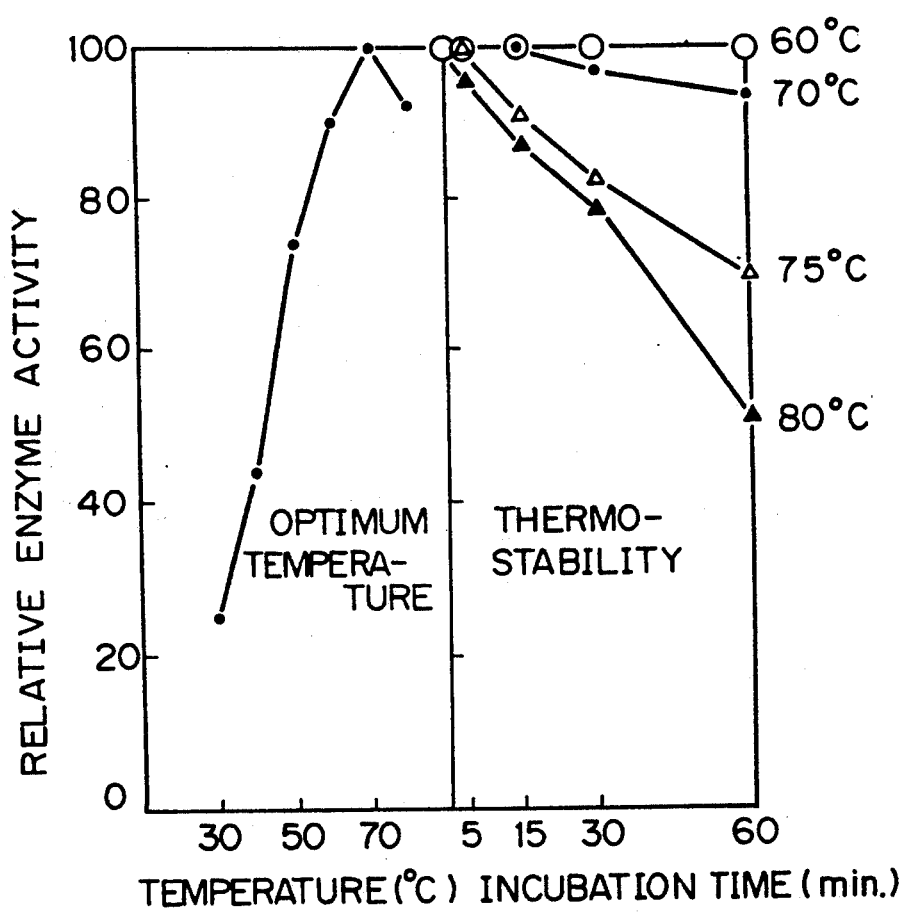
FIG. 3 shows graphs of the optimum temperature and thermostability of the present enzyme.

(3) Optimum temperature:

An optimum temperature of the present enzyme measured at pH 7.0 is 70° C., as shown in FIG. 3A. Where the enzyme is heated at temperatures of 60° C., 70° C., 75° C. or 80° C., the enzyme is not inactivated at 60° C. and 70° C. for 15 minutes, and after one hour, the enzyme exhibits a residual activity of not less than 90% at 70° C., 70% at 75° C., and 50% at 80° C., as shown in FIG. 3B.

(4) Molecular weight:

The enzyme exhibits a molecular weight of about 52,000±5,000, as determined by gel filtration using a Farmacia FPLS; column: Superose TM 12; and eluate: 50 mM acetic acid-sodium acetate (pH 5.0) containing 0.2 M NaCl. (5) UV spectrum The $\mu$ max in phosphate buffer is 275 nm, 190 nm.

(6) Elemental analysis:

C 59.4%; H 6.4%; N 15.3%.

The starch hydrolyzing activity of the present enzyme is measured as follows: A certain amount of an enzyme sample is added to 1% soluble starch, and after a reaction at a controlled pH and temperature for 5 minutes, the resulting amount of reducing sugar is measured by the 3,5-dinitrosalicylic acid method (DNS method) (Experimental Method of Starch and Related Sugars, ed. M. Nakamura, Gakkai Shuppan Center, p 43, 1986). One unit is defined as an enzyme acitivity which provides reducing sugars corresponding to 1 $\mu$mole glucose for one minute.

The raw starch hydrolyzing activity of the present enzyme is measured as follows: Raw starch is added to a buffer containing the enzyme to be measured, to a concentration of 1% starch, and the whole is shaken at 30° C. to 80° C. and pH 4.0 to 9.0 for 0 to 24 hours, and the resulting amount of sugar is determined using a calibration curve for glucose. The saccharification extent is expressed by dextrose equivalent (DE) value.

DE is the term used to characterize the degree of degradation of the starch, and is represented by the reducing power of the starch material as compared with pure dextrose which represents 100%.

To isolate microorganisms producing the present enzyme, first, microorganisms are isolated from microbial sources such as soil. Next, the isolated microorganisms are plated on a solid medium containing meat extract, peptone, and 2% wheat raw starch, and microorganisms which form a halo on the raw starchcontaining medium are selected. The selected microorganisms are then cultured in a liquid medium, and microorganisms exhibiting a raw starch-hydrolizing activity are selected. Thus, in accordance with the present invention, by using the above-procedures, a desired microorganism was isolated from a soil sample.

The taxonomical properties of the isolated microorganism were determined in accordance with Bergey's Manual of Determinative Bacteriology, 7th and 8th editions, and the microorganism was identified as a strain belonging to *Bacillus stearothermoohilus*, and was determined to be a new strain since this strain is different from known strains in that the isolated strain has an ability to hydrolyze raw starch. Accordingly, this strain was designated *Bacillus stearothermophilus* B-1, and deposited with the Fermentation Research Institute, Agency of Industrial Science and Technology, 1-3 Higashi 1-chome Tsukuba-shi, Ibaraki-ken, 305 Japan, as FERM P-10120 on June 30, 1988, and transferred to an international deposition under the Budapest treaty as ERRM BP-2440 on May 26, 1989.

The taxanomical properties of *B. stearothermoohilus* B-1 are as follows.

1. Microscopy (including electromicroscopy)
   Gram stain: positive
   Morphology: Rod
   Size: 0.6–1.6×2–3.5 $\mu$m
   Polymorphism: absent
   Motility: positive
   Flagella: absent
   Spores: oval, size 1–1.8 $\mu$m, present in end of cell
   Anti-acidity: negative
2 Observation of culture
   Bouillon agar plate: colonies of irregular size with a diameter of 5 mm, after 24 hours culturing, white colored, and with irregular edge.
   Bouillon agar slant: white, not fluidal
   Bouillon liquid: white turbidity, white precipitates.
   Bouillon gelatin stab: liquefying gelatin
   Litmus milk: acidic, coagulation
3. Physiological properties
   Reduction of nitrate: +
   MR test: −
   VP test: −
   Production of indole: −
   Production of hydrogen sulfide: −

Hydrolysis of starch: +
Utilization of citrate: −
Utilization of nitrate ($NO_3^-$): −
Utilization of ammonia ($NH_4^-$): +
Production of pigments: brown pigment slightly soluble in water
Catalase: +
Oxidase: ±
Range of conditions for growth
(pH): 5.5 to 8.0
(temperature): 45° C. to 75° C.
Behavior to oxygen: aerobic
O-F test: O 4. Acidification, gas formation and assimilation of sugars

| Sugar | Acid | Gas | Assimilation |
| --- | --- | --- | --- |
| L-Arabinose | + | − | + |
| D-Xylose | + | − | + |
| D-Glucose | + | − | + |
| D-Mannose | + | − | + |
| D-Fructose | + | − | + |
| D-Galactose | ± | − | ± |
| Maltose | ± | − | + |
| Sucrose | + | − | + |
| Lactose | − | − | − |
| Trehalose | ± | − | + |
| D-Sorbitol | − | − | − |
| D-Mannitol | + | − | + |
| Inositol | − | − | − |
| Glycerol | ± | − | ± |
| Starch | + | − | + |

5. Other properties
Raw starch hydrolyzing ability: Although the present strain forms a halo on a raw starch-containing agar medium, *Bacillus stearothermophilus* IFO 12550 does not form a halo on the same medium.

For the production of the thermostable amylase of the present invention, or for the use thereof as a source of thermostable amylase in a process for the production of oligo saccharides such as maltose and maltotriose according to the present invention, the above-mentioned thermostable amylase producer strain is preferably cultured in a liquid medium containing a carbon source and a nitrogen source. The carbon source includes various kinds of starch, starch hydrolyzates, corn meal, wheat flour, molasses and the like, which can be used alone or in combination. The concentration of these carbon sources is 0.1% to 30%, preferably 1% to 15%. The nitrogen source includes soybean flour, cotton seed meal, peptone, casein, meat extract, yeast extract, malt extract, inorganic ammonium salts, and inorganic nitrate salts. These nitrogen sources can be used alone or in combination. The concentration of the nitrogen sources is 0.05% to 20%, preferably 0.5% to 10%. Further, minor inorganic salts such as phosphates, magnesium salts, $FeSO_4$, KCl, $CaCl_2$ and the like, and/or minor organic nutrient sources such as amino acids, vitamins, and the like can be used.

A thermostable amylase producing strain of the present invention is cultured in the above-mentioned medium under an aerobic condition provided by shaking, or a combination of agitation and aeration, at a temperature of about 45° C. to 75° C., preferably 50° C. to 65° C., and at a pH of about 5.5 to 8.0, preferably 6.0 to 7.5, for 12 to 100 hours, preferably 24 to 72 hours.

During the culturing, thermostable amylase of the present invention extracellularly accumulates in the culture broth. For the isolation and purification of the desired amylase, the culture broth is centrifuged or filtered to eliminate cells, and the resulting cell-free liquid is used for the purification of the enzyme. In one embodiment, the cell-free broth is subjected to salting out using ammonium sulfate at 70% saturation, and the 70% saturation-precipi-tation fraction is then dissolved in a buffer and applied to a colum such as a Sephadex G-100 column, and eluted to recover an amylase active fraction. For further purification, a conventional procedure such as ion exchange chromatography may be used.

The present thermostable amylase is used to produce maltose or other oligo saccharides, and may be used in a purified form, or crude or partially purified form, such as a whole culture broth, cell-free supernatant or filtrate derived from the culture broth, ammonium sulfate precipitation fraction, precipitate obtained by organic solvent such as ethanol or acetone, Sephadex-purified product, and DEAE-Cellulose-purified product and the like. Also, an immobilyzed enzyme may be used. The enzyme reaction producing maltose or other oligo saccharides is carried out at a temperature of between room temperature and 70° C., preferably between 55° C. and 65° C., for example, at about 60° C., in a reaction medium at pH of 4.5 to 9.0, preferably a pH of 5 to 8, for example, at a pH of 7.2. The enzyme is used in an amount of 1 to 300 units per 1 g starch, although the amount can be controlled depending on reaction temperature used, acceptable reaction time, and the like. The reaction time is about 0.5 to 100 hours, most preferably 6 to 48 hours. The reaction medium is water or a buffer such as a phosphate buffer.

In a preferred embodiment of the above-mentioned enzyme reaction for the production of maltose or other oligosaccharides, raw starch is suspended in water at a concentration of about 10 to 50% and the suspension is heated to a temperature lower than a temperature at which the raw starch is gelatinyzed, for example, the above-mentioned temperature, and then the thermostable amylase of the present invention is added to the starch suspension. Alternatively, the enzyme may be added to the starch suspension before heating or during heating. Note, in this procedure, a conventionally used liquefying type α-amylase is not necessary because the viscosity of the suspension does not increase, and the debranching enzyme also is not necessary because the present thermostable enzyme alone can hydrolyze raw starch at a ratio of substantially 100%. Further, since the starch suspension has a tendency to precipitate, the suspension is preferably constantly or periodically stirred during the reaction.

As the raw starch, starches of any origin, such as wheat starch, rice starch, corn starch, potato starch, sweet potato starch, and the like may be used.

Maltose, maltotriose and other oligosaccharides can be isolated and purified by a well established conventional procedure.

EXAMPLES

The present invention will now be further illustrated by, but is by no means limited to, the following examples.

EXAMPLE 1

Culturing for Enzyme Production

*Bacillus stearothermochilus* B-1 was inoculated in a medium containing 0.5% meat extract, 1% Polypeptone, 0.5% NaCl, and 1% soluble starch, adjusted to a pH of 7.0 with NaOH, and cultured at 55° C. for 24 hours while shaking. After centrifugation of the broth to eliminate cells, the supernatant exhibited 1.06 units/ml of amylase activity.

EXAMPLE 2

Purification of Enzyme

The culture broth obtained as described in Example 1 was centrifuged at 10,000 rpm for 20 minutes to eliminate cells, and ammonium sulfate was added to the supernatant to a 70% saturation, and the whole was allowed to stand for 24 hours. After centrifugation at 10,000 rpm for 20 minutes, a precipitate of crude enzyme was obtained, the crude enzyme was dissolved in 10 mM phosphate buffer (pH 7.2), and the solution was centrifuged at 15,000 rpm for 20 minutes to eliminate insoluble matter. The obtained supernatant was subjected to gel filtration using Sephadex G-100, to obtain a fraction having amylase activity.

Next, the fraction having amylase activity was applied to DEAE Cellulose 32, and elution was carried out with a 10 mM phosphate buffer (pH 8.5) to obtain a fraction having amylase activity. The fraction having amylase activity was again applied to DEAE Cellulose 32, and elution was carried out with a 10 mM phosphate buffer (pH 7.2) to obtain a fraction having amylase activity. The fraction was dialyzed against pure water, followed by lyophilization to obtain an enzyme preparation. This enzyme preparation showed a single band in disk electrophoresis. The above-mentioned purification steps, corresponding yield, and specific activities are summarized in Table 1.

TABLE 1

| Enzyme fraction | Yield (%) | Specific activity (unit/mg protein) |
|---|---|---|
| Culture broth | 100 | 1.00 |
| 70% Ammonium sulfate fraction | 40 | 6.25 |
| Sephadex G-100 fraction | 24 | 7.20 |
| DEAE Cellulose fraction | 6.7 | 35.0 |

EXAMPLE 3

Measurement of Raw Starch Hydrolysation Ratio

Figure 1:
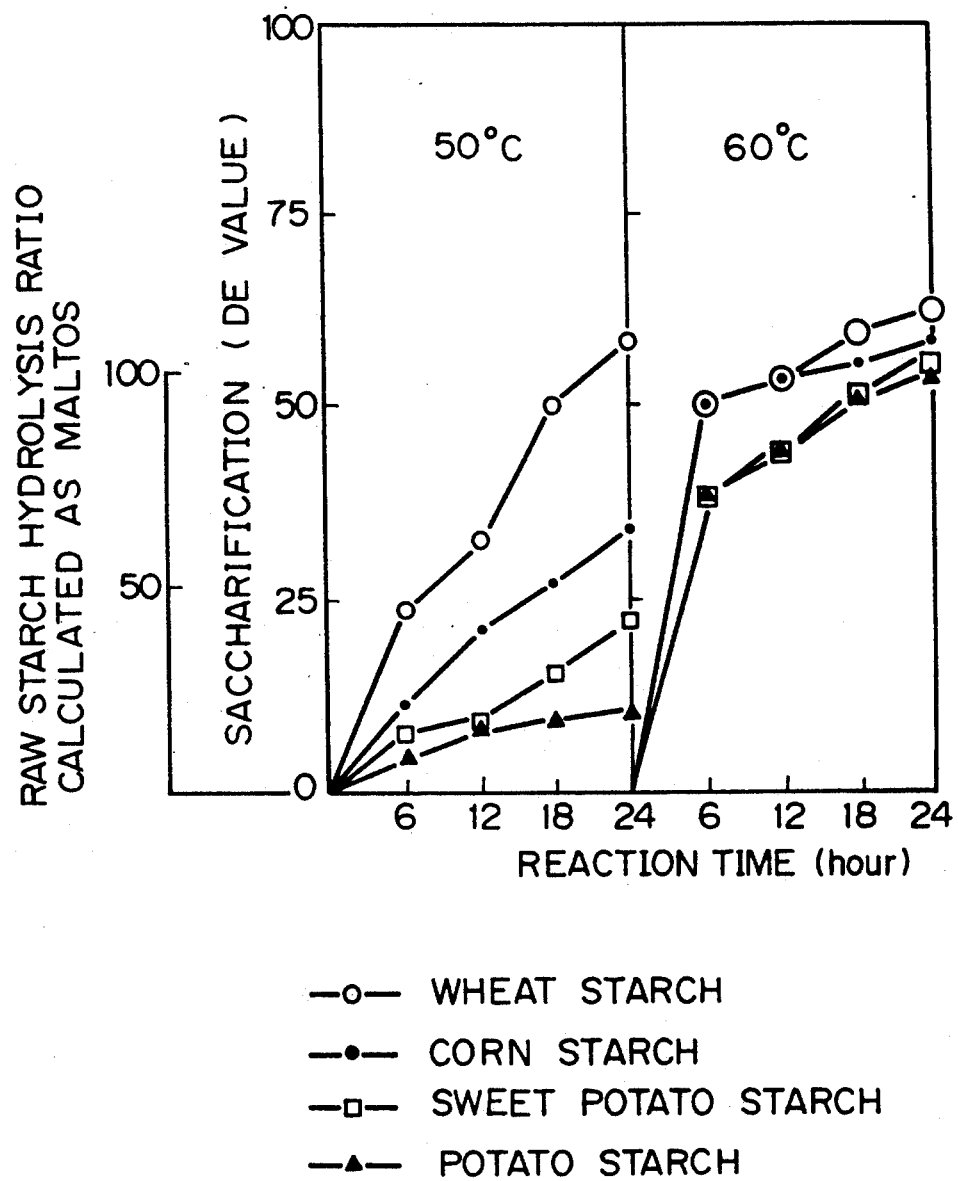
FIG. 1 shows graphs of the progress of the hydrolysis of starches of different origins by the present enzyme, at different temperatures.

First 40 mg of raw starch of different origins was put into a 50 ml conical flask, 4 ml of a phosphate buffer (pH 7.2) containing enzyme (5.925 units, 60° C.) was added to the flask, and the reaction mixture was shaken at 60° C. Samples were obtained at 6 hour-intervals, and were centrifuged at 1,000 rpm for 5 minutes. Each supernatant was diluted by an appropriate ratio, and the amount of reducing sugar was measured by the DNS method. The amount of reducing sugar was expressed by a DE value. The results are shown in FIG. 1. The composition of reducing sugars produced by the hydrolysis of raw starch was analyzed by HPLC using a Hitachi 665A-12LC apparatus; a detector: Waters Electronics Unit differential refractometer; a column: a Nakarai Cosmosil Packed column 4.6×150 mm; and an eluate: acetonitrile/water at a ratio of 75/25. Among the produced reducing sugars, the main component was maltose, followed by maltotriose and glucose, in this order in relation to the amounts thereof. Taking into consideration the DE value and the composition of the reducing sugars, the hydrolysis ratio of the raw starch was approximately 100% at a reaction temperature of 60° C.

EXAMPLE 4

Production of Reducing Sugars (1)

First, 5 g of corn starch was suspended in 15 ml of 0.1 M acetate buffer (pH 6.0), 5 ml of enzyme solution containing 50 units of the thermostable amylase of the present invention was added to the suspension, and the reaction mixture was shaken at 55° C. for 12 hours. The reaction mixture was then analyzed by HPLC using a Hitachi 665-12LC apparatus; a detector: a Waters Electronics Unit differential refractometer; a column: a Nakarai Cosmosil Packed column 4.6×150 mm; and an eluate: acetonitrile/water at a ratio of 75/25). Glucose, maltose, and maltotriose were formed at yields of 2.6%, 56.5%, and 32.8%, respectively, in relation to the amount of starting raw starch.

EXAMPLE 5

Production of Reducing Sugars (2)

Substantially the same procedure as described in Example 4 was repeated, except that wheat starch was used as the starting raw starch, and the reaction was carried out at 60° C. As a result, glucose, maltose and maltotriose were formed at yields of 2.1%, 51.3%, and 39.4%, respectively, in relation to the amount of starting raw starch.

EXAMPLE 6

Production of Reducing Sugars (3)

First, 5 g each of corn starch, potato starch, sweet potato starch, and wheat starch was weighed, and thereto was added 15 ml of 0.1 M acetate buffer (pH 6.0) containing 100 units of the thermostable amylase of present invention, and the reaction mixture were shaken at 60° C. for 24 hours. The compositions of the reaction mixtures, when analyzed by HPLC, are summarized in Table 2.

TABLE 2

| | Products | | |
|---|---|---|---|
| Starch | glucose | maltose | maltotriose |
| Corn starch | 3.2 | 50.7 | 36.5 |
| Potato starch | 3.7 | 52.8 | 33.4 |
| Sweet potato starch | 3.5 | 55.5 | 30.8 |
| Wheat starch | 2.9 | 54.3 | 32.7 |

As seen from the above, by using the thermostable amylase of the present invention capable of hydrolyzing raw starch to produce maltose and maltotriose, the galatinyzation and liquefication steps can be omitted, and the debranching enzyme is not necessary, and thus this is an advantageous industrial process from the viewpoint of apparatus use, energy, and agents.

We claim:

1. An isolated thermostable amylase produced by Bacillus having the following properties:
   (A) action: acting on raw starch to produce substantially maltose and maltotriose;
   (B) optimum pH: about 6.0;
   (C) stable pH: after incubation at a pH of 5 to 8 for one hour at 22° C., having a residual activity of at least 95%;
   (D) optimum temperature: 70° C.;
   (E) thermostability: said amylase is not substantially inactivated by incubation at 60° C. to 70° C. for 15 minutes; and after incubation at 70° C. for one hour, said amylase having a residual activity of at least 90%; and
   (F) molecular weight: 52,000±5,000 as determined by gel filtration.

2. The isolated thermostable amylase according to claim 1 produced by *Bacillus stearothermophilus*.

* * * * *